US00PP12659P2

(12) United States Plant Patent
Dekker

(10) Patent No.: US PP12,659 P2
(45) Date of Patent: May 28, 2002

(54) CHRYSANTHEMUM PLANT NAMED 'EUROBELLE'

(75) Inventor: Niek Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 09/653,172

(22) Filed: Aug. 31, 2000

(51) Int. Cl.[7] ..... A01H 5/00
(52) U.S. Cl. ..... Plt./288
(58) Field of Search ..... Plt./288

(56) References Cited

PUBLICATIONS

UPOV–ROM GTITM Computer Database 2001/04, GTI Jouve Retrieval Software, citation for 'Eurobelle'.*

* cited by examiner

*Primary Examiner*—Anne Marie Grünberg
(74) *Attorney, Agent, or Firm*—C. A. Whealy

(57) ABSTRACT

A distinct cultivar of Chrysanthemum plant named 'Eurobelle', characterized by its white decorative inflorescences with green centers; dark green foliage; early response time; and good post-production longevity.

2 Drawing Sheets

BACKGROUND OF THE INVENTION

The present invention relates to a new and distinct cultivar of Chrysanthemum plant, botanically known as *Dendranthema grandiflora* and referred to by the cultivar name Eurobelle.

The new Chrysanthemum is a product of a planned breeding program conducted by the Inventor in Hensbroek, The Netherlands. The objective of the program is to create and develop new Chrysanthemum cultivars with interesting inflorescence forms, attractive floret colors, and good post-production longevity.

The new Chrysanthemum originated from a cross by the Inventor of the Inventor's proprietary selection of *Dendranthema grandiflora* identified as K.O.5001.06 as the female, or seed, parent with the Inventor's proprietary selection of *Dendranthema grandiflora* identified as K.O.5001.31 as the male, or pollen, parent. The new Chrysanthemum was discovered and selected by the Inventor as a plant within the progeny of the stated cross in a controlled environment in Hensbroek, The Netherlands in 1996. The selection of the new Chrysanthemum was based on its inflorescence form and ray floret coloration.

Asexual reproduction of the new Chrysanthemum by terminal cuttings harvested in Hensbroek, The Netherlands, has shown that the unique features of this new Chrysanthemum are stable and reproduced true to type in successive generations.

BRIEF SUMMARY OF THE INVENTION

The cultivar Eurobelle has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Eurobelle'. These characteristics in combination distinguish 'Eurobelle' as a new and distinct cultivar:

1. White decorative inflorescences with green centers.

2. Dark green foliage.
3. Early response time.
4. Good post-production longevity.

Plants of the new Chrysanthemum differ from plants of the female parent, the selection K.O.5001.06, primarily in ray floret color as the female parent has pink-colored ray florets. In addition, plants of the new Chrysanthemum are more vigorous than plants of the female parent. Plants of the new Chrysanthemum differ from plants of the male parent, the selection K.O.5001.31, primarily in inflorescence form as the male parent has semi-decorative inflorescences. In addition, inflorescences of plants of the new Chrysanthemum form very little pollen whereas inflorescences of plants of the male parent form abundant pollen.

Plants of the new Chrysanthemum can be compared to the Chrysanthemum cultivar Calabria, not patented. In side-by-side comparisons conducted by the Inventor in Hensbroek, The Netherlands, plants of the new Chrysanthemum and the cultivar Calabria differ in the following characteristics:

1. Plants of the new Chrysanthemum have longer flowering stems than plants of the cultivar Calabria.
2. Inflorescence centers of plants of the new Chrysanthemum are more green in color than inflorescence centers of plants of the cultivar Calabria.
3. Plants of the new Chrysanthemum have longer post-production longevity than plants of the cultivar Calabria.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Chrysanthemum.

The photograph on the first sheet comprises a side perspective view of a typical flowering stem of 'Eurobelle'.

The photograph at the top of the second sheet comprises a close-up view of typical inflorescences of 'Eurobelle'.

The photograph at the bottom of the second sheet comprises a close-up view of the upper and lower surfaces of typical leaves of 'Eurobelle'.

DETAILED BOTANICAL DESCRIPTION

In the following description, color references are made to The Royal Horticultural Society Colour Chart except where general terms of ordinary dictionary significance are used. The following observations and measurements describe plants grown in Hensbroek, The Netherlands, under commercial practice in a glass-covered greenhouse. Rooted cuttings were planted mid-February, 2000, in soil beds and given about 21 long days/short nights before starting the photoinductive short day/long night treatment. Average day and night temperatures were about 20 and 18° C., respectively, and light level was about 30,000 lux. Measurements and numerical values represent averages for typical flowering stems.

Botanical classification: *Dendranthema grandiflora* cultivar Eurobelle.

Commercial classification: Decorative-type cut Chrysanthemum.

Parentage:

*Female, or seed, parent.*—Proprietary selection of *Dendranthema grandiflora* identified as K.O.5001.06, not patented.

*Male, or pollen, parent.*—Proprietary selection of *Dendranthema grandiflora* identified as K.O.5001.31, not patented.

Propagation:

*Type.*—Terminal tip cuttings.

*Time to initiate and develop roots, summer.*—About 14 days at temperatures about 20° C.

*Time to initiate and develop roots, winter.*—About 16 days at temperatures about 20° C.

*Rooting habit.*—Fine, fibrous and well-branched.

Plant description:

*Appearance.*—Herbaceous decorative-type cut Chrysanthemum, typically grown as a spray-type.

*Growth rate.*—Moderate growth rate; vigorous.

*Stem description.*—Length: About 70 to 80 cm. Strength: Strong. Aspect: Upright. Color: 146B to 146C.

*Foliage description.*—Arrangement: Alternate. Quantity of leaves per flowering stem: About 18 to 23. Length: About 11.5 cm. Width: About 6.5 cm. Apex: Acute. Base: Acuminate. Margin: Palmately lobed. Texture: Rough; both surfaces pubescent. Petiole length: About 2.5 cm. Color: Young foliage upper surface: 137A to 147A. Young foliage lower surface: 137B to 137C. Mature foliage upper surface: 137A to 137B. Mature foliage lower surface: 137C to 137D. Venation upper and lower surfaces: 137D. Petiole: 137D.

Inflorescence description:

*Appearance.*—Decorative-type inflorescence form. Inflorescences borne on terminals, arising from leaf axils. Disc and ray florets arranged acropetally on the receptacle.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about 53 days later.

*Post-production longevity.*—Cut flowering stems of the new Chrysanthemum last about two to three weeks after harvesting.

*Quantity of inflorescences per flowering stem.*—About 13 to 18.

*Inflorescence size.*—Diameter: About 7 cm. Depth (height): About 2.5 cm. Diameter of disc: About 8 mm.

*Inflorescence buds.*—Length: About 9 mm. Diameter: About 11.5 mm. Shape: Flat spherical. Color: 138A.

*Ray florets.*—Length, largest florets: About 3.5 cm. Width, largest florets: About 1.3 cm. Shape: Elongated oblong; concave. Apex: Praemorse. Base: Fused, tubular. Texture: Smooth, glabrous. Number of ray florets per inflorescence: About 180. Color: When opening, upper and lower surfaces: Apex, 142B; base, 155B. Fully opened, upper and lower surfaces: Apex, 155B; base, 144C to 144D.

*Disc florets.*—Shape: Tubular. Length: About 5 mm. Width: About 1.5 mm. Number of disc florets per inflorescence: About 10. Color: Immature: Close to 145A to 145B. Mature: Apex, 145A; mid-section, 155B; and base, 151C.

*Peduncles.*—Length, terminal peduncle: About 8 cm. Length, fourth peduncle: About 13 cm. Diameter: About 2.5 mm. Angle: About 60° to main stem. Texture: Pubescent. Color: 137C to 137D.

*Reproductive organs.*—Androecium: Present on disc florets only. Anther color: 151B. Pollen amount: Scarce. Pollen: 23A. Gynoecium: Present on both ray and disc florets. Stigma length: About 1 mm. Stigma diameter: About 0.3 mm. Stigma color: Apex, 151B; base, 144C to 144D.

*Seed.*—Seed production has not been observed.

Disease resistance: Resistance to known Chrysanthemum diseases has not been observed on plants of the new Chrysanthemum grown under commercial conditions.

It is claimed:

1. A new and distinct cultivar of Chrysanthemum plant named 'Eurobelle', as illustrated and described.

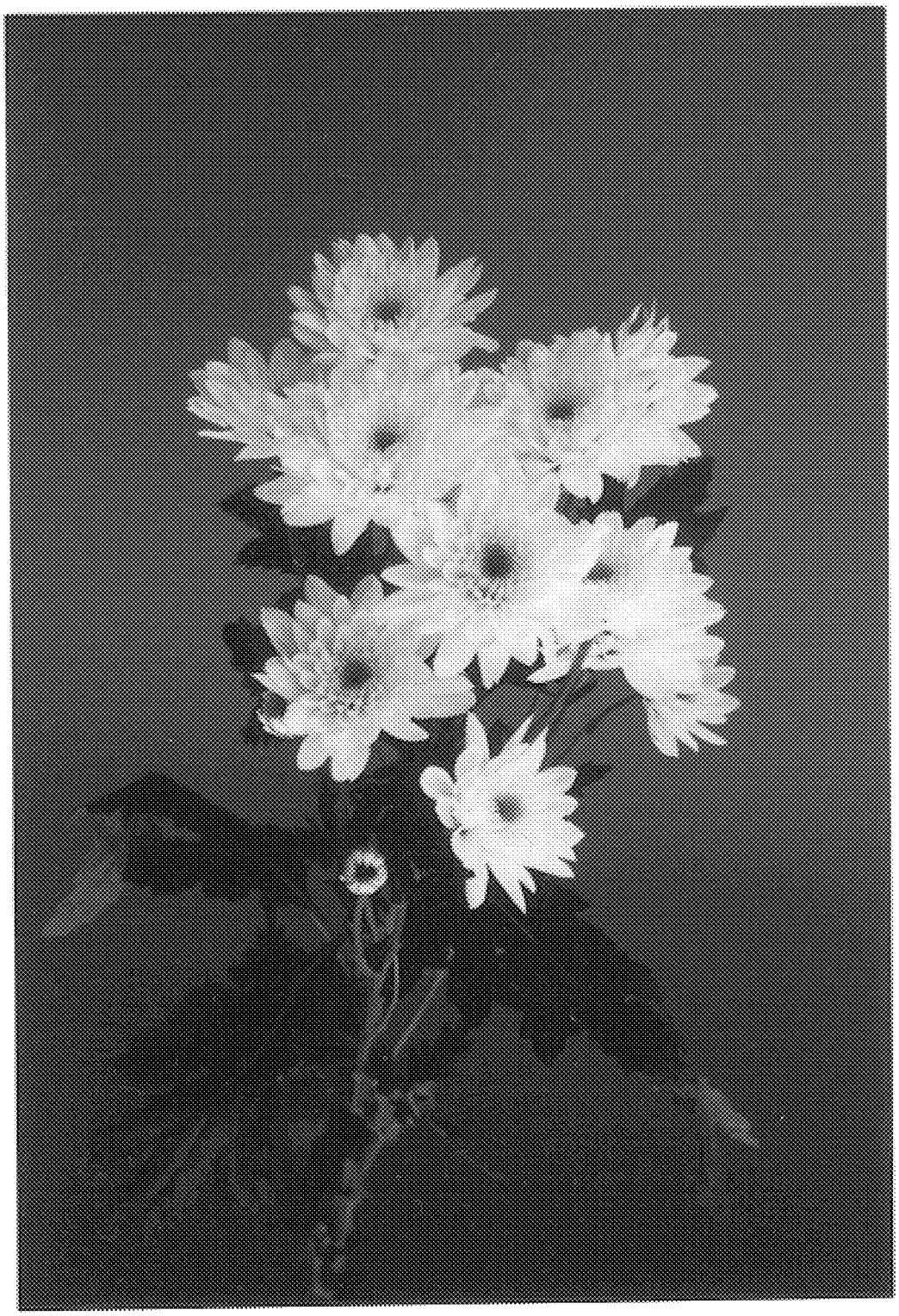

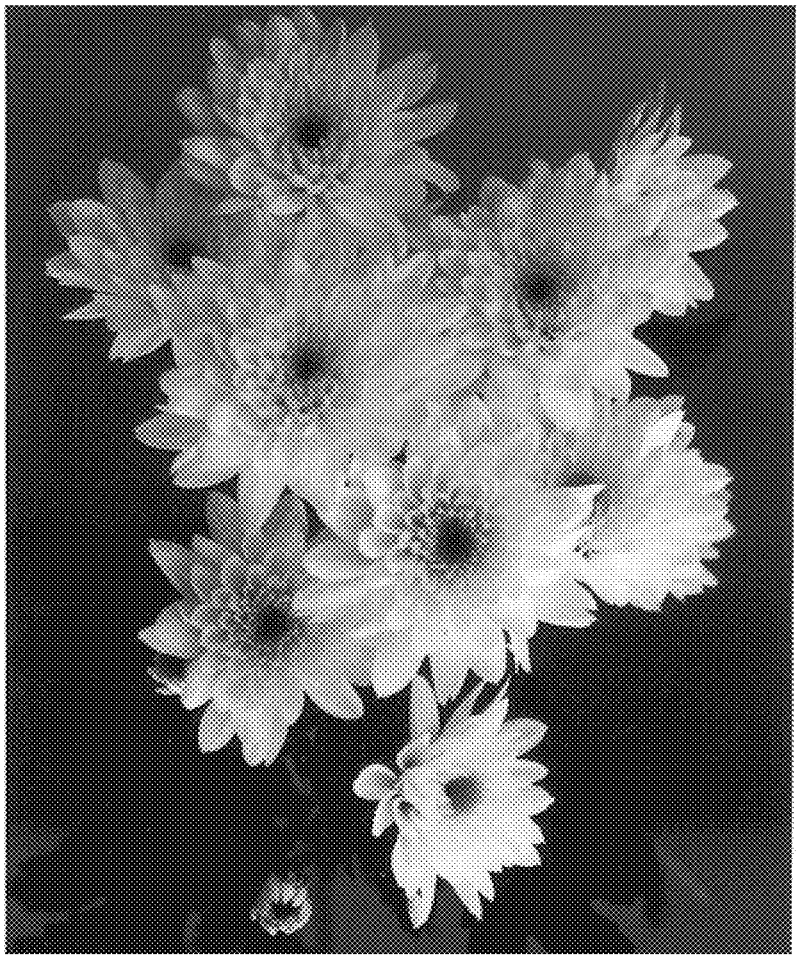
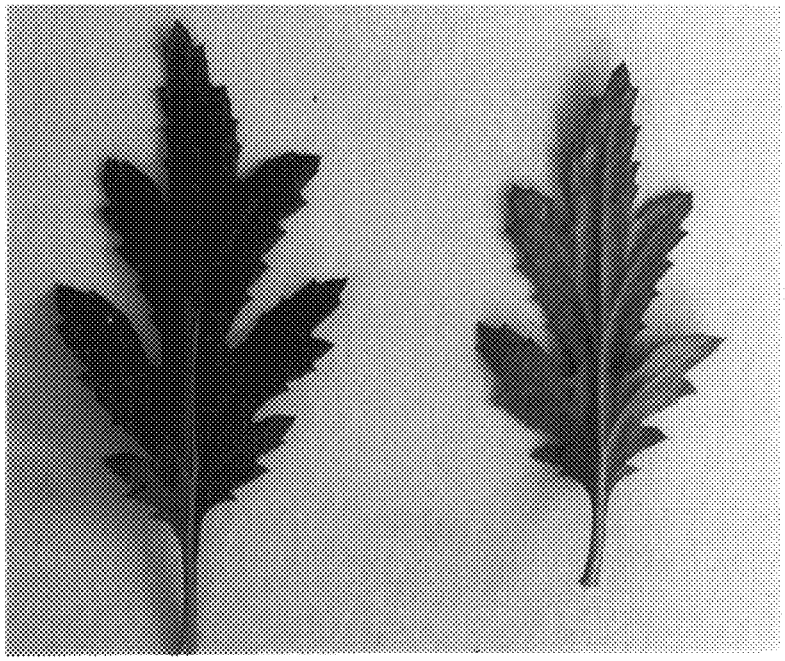

* * * * *